(12) United States Patent
Beneyto-Ferre

(10) Patent No.: US 10,791,967 B2
(45) Date of Patent: Oct. 6, 2020

(54) METHOD AND DEVICE FOR SIGNALIZING A WALKING OR RUNNING SPEED TO A RUNNER OR WALKER

(71) Applicant: PUMA SE, Herzogenaurach (DE)

(72) Inventor: Jordi Beneyto-Ferre, Nuremberg (DE)

(73) Assignee: PUMA SE, Herzogenaurach (DE)

( * ) Notice: Subject to any disclaimer, the term of this patent is extended or adjusted under 35 U.S.C. 154(b) by 0 days.

(21) Appl. No.: 16/467,324

(22) PCT Filed: Dec. 9, 2016

(86) PCT No.: PCT/EP2016/002082
§ 371 (c)(1),
(2) Date: Jun. 6, 2019

(87) PCT Pub. No.: WO2018/103812
PCT Pub. Date: Jun. 14, 2018

(65) Prior Publication Data
US 2019/0328286 A1 Oct. 31, 2019

(51) Int. Cl.
| | | |
|---|---|---|
| *G08B 1/08* | (2006.01) | |
| *A61B 5/11* | (2006.01) | |
| *H04W 4/029* | (2018.01) | |
| *A61B 5/00* | (2006.01) | |
| *G01S 19/52* | (2010.01) | |

(Continued)

(52) U.S. Cl.
CPC .......... *A61B 5/1118* (2013.01); *A61B 5/6804* (2013.01); *A61B 5/742* (2013.01); *G01S 19/52* (2013.01); *G08B 5/36* (2013.01); *H04M 1/72569* (2013.01); *H04W 4/029* (2018.02)

(58) Field of Classification Search
CPC ..... A61B 5/1118; A61B 5/742; A61B 5/6804; A61B 5/6898; A61B 5/7445; A61B 5/1112; A61B 5/68; A61B 5/0015; H04M 1/72569; G08B 5/36; G01S 19/52; G01S 19/19; H04W 4/029; G09B 19/003; G09B 5/02; A63B 24/0062; G06Q 10/06; G06Q 10/0639
USPC ........ 340/539.13, 539.1, 573.1, 691.6; 2/69; 362/606, 103
See application file for complete search history.

(56) References Cited

U.S. PATENT DOCUMENTS

| | | | |
|---|---|---|---|
| 2010/0234714 A1* | 9/2010 | Mercier | A61B 5/02438 600/388 |
| 2010/0292599 A1* | 11/2010 | Oleson | A63B 24/0062 600/519 |

(Continued)

FOREIGN PATENT DOCUMENTS

| | | |
|---|---|---|
| EP | 2407218 A2 | 1/2012 |
| WO | 2016074689 A1 | 5/2016 |

*Primary Examiner* — Ahn V La
(74) *Attorney, Agent, or Firm* — Lucas & Mercanti, LLP; Klaus P. Stoffel

(57) ABSTRACT

A method and a device for signalizing a walking or running speed to a runner or walker during walking or running, wherein the runner or walker wears a garment. To conveniently inform the walker or runner about his or her actual walking or running speed, the method includes: a) Determining the actual speed by a speedometer which is worn or carried by the runner or walker; b) Transferring of the actual speed into a light signal, wherein the light signal corresponds to the speed; c) Displaying the light signal by a light emitting element which is attached to the or integrated into the garment.

6 Claims, 2 Drawing Sheets

(51) Int. Cl.
*G08B 5/36* (2006.01)
*H04M 1/725* (2006.01)

(56) References Cited

U.S. PATENT DOCUMENTS

| | | |
|---|---|---|
| 2014/0078773 A1 | 3/2014 | Curran |
| 2015/0370320 A1* | 12/2015 | Connor ................ A61B 5/6831 345/173 |
| 2016/0038083 A1* | 2/2016 | Ding .................... A61B 5/6804 600/388 |
| 2016/0317101 A1 | 11/2016 | Li |

* cited by examiner

METHOD AND DEVICE FOR SIGNALIZING A WALKING OR RUNNING SPEED TO A RUNNER OR WALKER

The present application is a 371 of International application PCT/EP2016/002082, filed Dec. 9, 2016, the priority of this application is hereby claimed and this application is incorporated herein by reference.

BACKGROUND OF THE INVENTION

The invention relates to a method for signalizing a walking or running speed to a runner or walker during walking or running, wherein the runner or walker wears a garment, wherein the method comprises:
- a) Determining the actual speed by a speedometer which is worn or carried by the runner or walker;
- b) Calculating the difference speed between the actual speed and a predetermined reference speed;
- c) Transferring of the difference speed into a light signal, wherein the light signal corresponds to the difference speed;
- d) Displaying the light signal by means of a light emitting element, wherein in step c) the transfer takes place by defining at least one predetermined color of the light signal in dependency on the difference speed, wherein a first color is displayed if the actual speed is below a first predetermined percentage of the reference speed and wherein a second color, which is different from the first color, is displayed if the actual speed is above a second predetermined percentage of the reference speed, wherein no light signal or a third color, which is different from the first color and from the second color, is displayed if the actual speed is above the first predetermined percentage of the reference speed and below the second predetermined percentage of the reference speed, wherein the speedometer comprises or is an electronic device with a GPS module, wherein the actual speed is determined by means of a change in the position detected by the GPS module and the time elapsed during the position change, wherein a GPS module is used which is part of a mobile phone (the term "smart phone" is used herein equivalently).

Especially during sport activities it is often of interest for a runner or walker to know the actual walking or running speed. Speedometers are well known in the art, for example designed like a watch. In many cases it disturbs the sport activity when the walker or runner must read the display of the speedometer to get the desired information concerning his or her actual speed.

A method of the above mentioned kind is known from EP 2 407 218 A2. As light emitting element an output device with a visual display is used which makes it complicated to read the actual speed during sporting activities.

Another method is known from US 2014/0078773 A1. Here, an illuminated vest is disclosed which is equipped with an optical fiber structure. An optical signal is provided to the wearer if his or her cadence during sporting activities is too slow. Other solutions are known from US 2016/0317101 A1 and from WO 2016/074689 A1.

SUMMARY OF THE INVENTION

Thus, it is an object of the invention to propose a method by which it is possible to transfer the information concerning the actual speed of a walker or runner to the same in a convenient manner so that walking or running is not disturbed or hindered.

The solution of this object according to the invention is characterized in that displaying the light signal according to above step d) takes place by a light emitting element in the form of a glass fiber or an optical fiber, which is attached to the or integrated into the garment.

That is, according to the invention the difference speed to a set (predetermined) given value is communicated by means of a light emitting element which is connected with the garment. Specifically, a glass fiber and optical fiber respectively is used as the light emitting element which preferably runs down the arm sleeves of the garment—if the garment is a jacket or the like—so that the walker or runner can have an easy view to the light emitting element. It is not necessary to read a display of a speedometer to get the information about the actual speed of the walker or runner. It becomes specifically easy to monitor in a convenient manner if a desired set speed of the walker or runner is kept.

While a jacket, especially a running jacket, or the like is preferred it is however also possible to apply the concept according to the present idea to other garments like for example a running trouser or the like.

The speed determination can be carried out by an app (software application) in the mobile phone. Also, the transferring of the actual speed or of the difference speed into the light signal can be carried out by an app in the mobile phone.

The method according to the invention proposes that the transfer takes place by defining at least one predetermined color of the light signal in dependency on the difference speed. Thus, the walker or runner can easily get the information about his or her actual speed by simply watching the actual color of the light emitting element.

The first predetermined percentage and/or the second predetermined percentage is preferably between 1% and 10%.

In addition no light signal is displayed if the actual speed is above the first predetermined percentage of the reference speed and below the second predetermined percentage of the reference speed. This has to be understood in such a manner that no signal is displayed if the actual speed is within a tolerance which is defined by the first percentage of the reference speed below the same as the lower limit and the second percentage of the reference speed above the same as the upper limit. Becoming slower than the lower limit will result in the display of the first color, becoming faster than the upper limit will result in the display of the second color.

That is, as long the walker or runner keeps a speed which is within a defined limit of tolerance no light signal is given via the light emitting element. If the speed of the walker or runner is reduced below the mentioned first percentage a first color (preferably: red) is displayed by the light emitting element (preferably by the glass fiber or optical fiber); the message to the walker or runner is: too slow. If the speed of the walker or runner is increased above the mentioned second percentage a second color (preferably: blue) is displayed by the light emitting element (preferably by the glass fiber or optical fiber); the message to the walker or runner is: too fast or fast enough.

As an alternative to displaying no light signal in the mentioned case it can also be taken into consideration that a third color, which is different from the first color and from the second color, is displayed if the actual speed is above the first predetermined percentage of the reference speed and below the second predetermined percentage of the reference speed.

That is, for example a red light signal is given in the case "too slow" and a blue light signal can be given in the case "faster than the upper tolerance limit". If the speed is within the tolerance a green light signal can be given, saying "speed within the set range".

So the walker or runner can easily keep a desired speed without reading any display of a speedometer.

A device for a runner or walker for signalizing a walking or running speed to the runner or walker during walking or running, can be characterized in that it comprises:
- a garment worn by the runner or walker during running or walking,
- at least one light emitting element which is attached to the or integrated into the garment,
- a receiving chamber or holding device for receiving or holding of a mobile phone which comprises a GPS module,
- a control element for controlling the activation of the at least one light emitting element in accordance with a signal emitted by the mobile phone and
- connection means for connecting the control element with the mobile phone,
- wherein the mobile phone or the control element comprises a speedometer for measuring the actual speed of the runner or walker.

The communication between the mobile phone and the control element which controls the light emitting elements occurs preferably wireless. The connection means comprise preferably elements for establishing a Blue Tooth connection which needs not to be described in detail here as it is well known in the art.

The receiving chamber is preferably a pocket in the inner side of the garment. Alternatively, another holding device can be used to keep the mobile phone in place.

The at least one light emitting element is preferably an optical fiber which is fixed to the garment, especially to arm sleeves of the garment.

Each one single light emitting element can be arranged in the left and in the right region of the garment.

The garment has preferably two arm sleeves which reach down at least to the elbow of the runner or walker.

This method steps are preferably repeated and carried out periodically to show a permanent signal to the walker or runner concerning his or her actual speed.

The garment is preferably a runner's jacket. However, the concept according to the present idea can of course be also applied to other garments like for example a running trouser.

Thus, the invention is basing on the idea that a smart phone with its GPS navigation function is used to deliver an effective tool for a runner or walker to get information concerning his or her actual speed. The information is communicated by means of optical signals.

Thus, it is an important aspect of the concept of the present invention that a smart phone is used, especially to assist during physical training (running). Beneficially, two distinct optical elements (optical fibers/glass fibers/electroluminescent element) are anchored in a garment on the sleeves of the same to make the speed information visible in an easy manner.

The optical elements (optical fibers/glass fibers) are connected with a Blue Tooth device which communicates with the smart phone which is worn during the physical training. According to the situation and controlled by the smart phone light is emitted into the distinct optical fibers by a control element which gets its information via Blue Tooth from the smart phone. So, an actual speed and specifically the difference between an actual speed and a set (predetermined) speed can be displayed in the mentioned manner.

While the present invention is here referred to a walker or runner who is wearing the garment in question it is of course also applicable and claimed for all athletes who carry out a sports with a certain speed or velocity like a skier or cyclist.

BRIEF DESCRIPTION OF THE DRAWING

In the drawings an embodiment of the invention is shown.

DETAILED DESCRIPTION OF THE INVENTION

Figure 1:
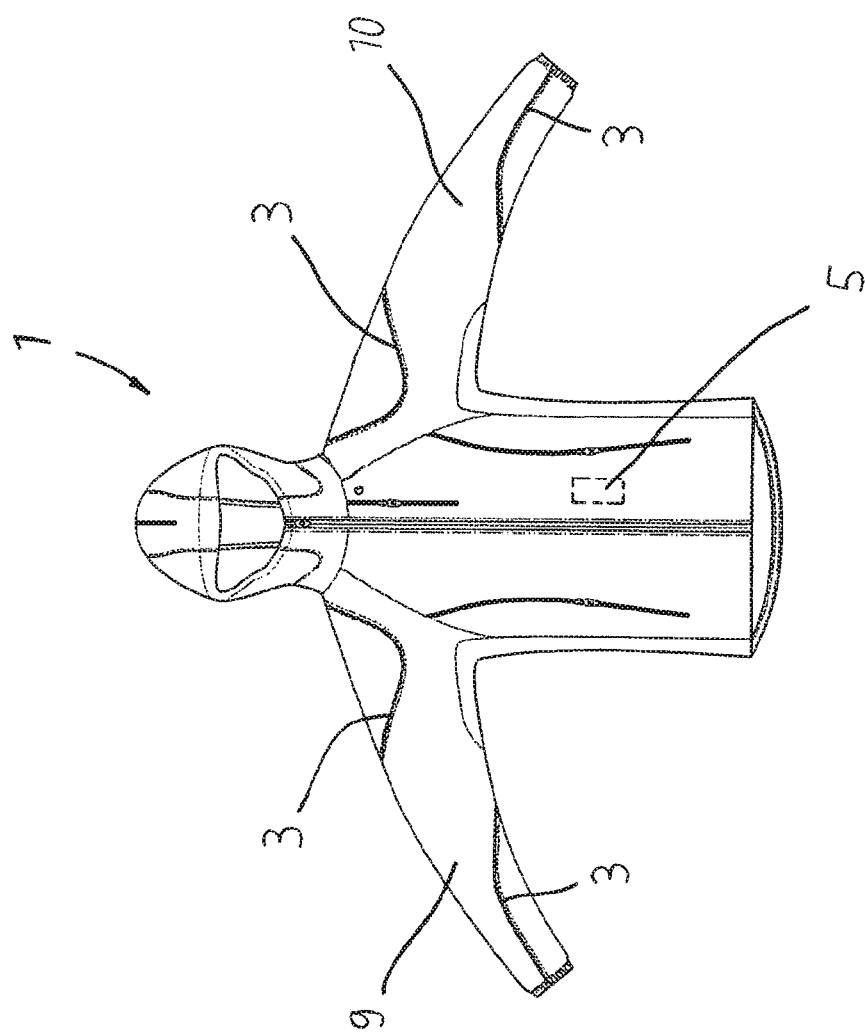
FIG. 1 shows the front view of a sports garment being a running jacket and
FIG. 2 shows schematically a part of the sports garment according to the invention.

In FIG. 1 a garment 1 being a runner's jacket is shown which has two (long) arm sleeves 9 and 10. In the inner of the garment 1 a receiving chamber 6 (see FIG. 2) is arranged in which a mobile phone 5 is inserted. A light emitting element 3 being an optical fiber is arranged in the garment 1 (or two separate light emitting elements 3) which extend in the sleeve region of the garment 1.

Figure 2:
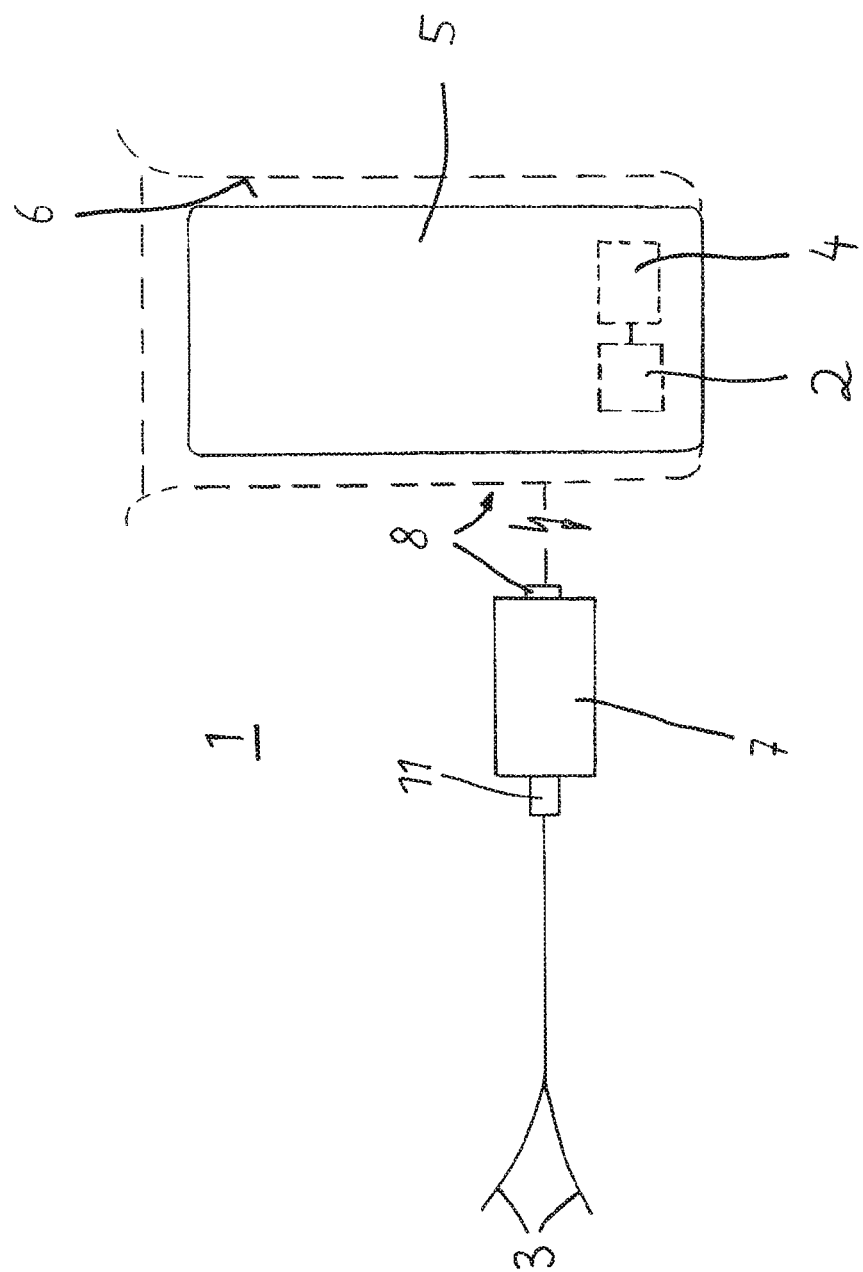

In FIG. 2 details of the arrangement are shown schematically. The receiving chamber 6 in the garment 1 is shown in which the smart phone 5 is inserted. The smart phone 5 has a GPS module 4, as known in the art, i.e. the exact position of the wearer of the smart phone 5 can be detected. The GPS module 4 is connected with a speedometer 2 (the speedometer 2 can be a part of the smart phone 5, as depicted, or can be a part of the control element 7, see below). The speedometer 2 receives permanently the change of the location of the smart phone 5 by means of the GPS module 4 and can calculate by means of an internal clock the actual speed ($v=\Delta s/\Delta t$, with $\Delta s$ being the difference in location in m and $\Delta t$ being the time difference in s which elapsed while the difference of location took place).

The smart phone 5 can communicate via connection means 8 (being a Blue Tooth connection in the present case) with a control element 7 which is mounted in the garment 1.

For displaying the actual speed v to the walker or runner or the actual difference between the actual speed and a set predetermined speed (which can be calculated in the smart phone 5 or in the control element 7) the signal is communicated via the connection means 8 to the control element 7. The control element 7 has a light emitting diode (LED) 11 which can be switched or influenced by the control element 7. The LED 11 is connected with the light emitting element 3. The LED 11 is specifically designed to emit light of different colors according to the control signal for the LED.

Consequently, according to the actual speed v of the walker or runner a light signal can be output to the walker or runner via the light emitting element 3.

As a preferred embodiment of the invention the light emitting element 3 is designed as a glass fiber/optical fiber which is integrated or anchored into the sleeves 9, 10 of the garment 1.

As said, the control element 7 can be designed to influence the color of the light emitting diode 11. Thus, a signal being a color or color change can be given to the user of the system which correlates with the actual speed v of the user or a difference speed between the actual speed and a set speed value.

REFERENCE NUMERALS

1 Garment
2 Speedometer

3 Light emitting element
4 GPS module
5 Mobile phone/smart phone
6 Receiving chamber
7 Control element
8 Connection means
9 Arm sleeve
10 Arm sleeve
11 Light Emitting Diode
v Actual running/walking speed
$v_0$ Reference speed
$\Delta v$ Difference speed $(v-v_0)$

The invention claimed is:

1. A method for signalizing a walking or running speed to a runner or walker during walking or running, wherein the runner or walker wears a garment, wherein the method comprises:
   a) Determining the actual speed by a speedometer which is worn or carried by the runner or walker;
   b) Calculating the difference speed between the actual speed (v) and a predetermined reference speed;
   c) Transferring of the difference speed into a light signal, wherein the light signal corresponds to the difference speed;
   d) Displaying the light signal by means of a light emitting element,
wherein in step c) the transfer takes place by defining at least one predetermined color of the light signal in dependency on the difference speed,
wherein a first color is displayed if the actual speed is below a first predetermined percentage of the reference speed and
wherein a second color, which is different from the first color, is displayed if the actual speed is above a second predetermined percentage of the reference speed,
wherein no light signal or a third color, which is different from the first color and from the second color, is displayed if the actual speed is above the first predetermined percentage of the reference speed and below the second predetermined percentage of the reference speed,
wherein the first predetermined percentage and the second predetermined percentage are between 1% and 10%,
wherein the speedometer comprises or is an electronic device with a GPS module, wherein the actual speed is determined by means of a change in the position detected by the GPS module and the time elapsed during the position change, wherein a GPS module is used which is part of a mobile phone, wherein
displaying the light signal according to step d) takes place by a light emitting element in the form of a glass fiber or an optical fiber, which is attached to the or integrated into the garment.

2. The method according to claim 1, wherein the speed determination is carried out by an app in the mobile phone.

3. The method according to claim 1, wherein the transferring of the difference speed into the light signal is carried out by an app in the mobile phone.

4. The method according to claim 1, wherein the first color is red.

5. The method according to claim 1, wherein the second color is blue.

6. The method according to claim 1, wherein the third color is green.

* * * * *